United States Patent [19]

Higley

[11] 4,160,769

[45] Jul. 10, 1979

[54] OXIDATION OF KETONES TO ESTERS

[75] Inventor: David P. Higley, Katonah, N.Y.

[73] Assignee: Union Carbide Corporation, New York, N.Y.

[21] Appl. No.: 859,924

[22] Filed: Dec. 12, 1977

[51] Int. Cl.$^2$ .................. C07D 313/04; C07D 309/08
[52] U.S. Cl. .................................. 260/343; 260/343.5
[58] Field of Search ............................ 260/343, 343.5

[56] References Cited

U.S. PATENT DOCUMENTS

| | | | |
|---|---|---|---|
| 2,362,439 | 11/1944 | Ruzicka et al. ........................ | 260/343 |
| 2,462,337 | 8/1946 | Shechter ............................. | 260/343.5 |
| 3,428,656 | 2/1969 | Weiss et al. .......................... | 260/343 |
| 3,577,216 | 4/1971 | Weiss et al. ......................... | 260/526 R |
| 3,590,080 | 6/1971 | Beesley et al. ....................... | 260/343 |

OTHER PUBLICATIONS

Pure and Applied Chemistry, vol. 1, Nos. 2–3, 1961, Butterworths, London.
Takayama et al., 14219x, Chemical Abstracts, vol. 73, 1970.

*Primary Examiner*—Natalie Trousof
*Assistant Examiner*—Jane T. Fan
*Attorney, Agent, or Firm*—Bernard Francis Crowe

[57] ABSTRACT

Cyclic ketones can be oxidized in high yields to the corresponding cyclic esters with hydrogen peroxide, selenium dioxide catalyst and a base. By-products are held to a minimum.

12 Claims, No Drawings

OXIDATION OF KETONES TO ESTERS

BACKGROUND OF THE INVENTION

This invention pertains to the selective oxidation of cyclic ketones to the corresponding lactones and more particularly to the use of hydrogen peroxide, selenium dioxide and a base.

Lactones are used directly for the synthesis of polyesters, polyurethanes, and the like and indirectly for the production of lactams which are in turn converted to polyamides. Epsiloncaprolactone is a prime example of this class of lactones serving as a starting material for the production of poly(epsilon-caprolactones), polyurethane elastomers and polyamides, such as, nylon-6. The synthesis of lactones in general and epsiloncaprolactone in particular has therefore been the subject of many research efforts.

The oxidation of cyclic ketones to cyclic lactones was discovered in 1899 and has since been known as the Baeyer-Villiger Reaction, although it has been broadened to include acyclic ketones. The oxidizing agents used in this reaction have included permonosulfuric acid (Caro's Acid), perbenzoic acid, monoperphthalic acid, peracetic acid and trifluoroperacetic acid. The selenium dioxide-catalyzed reaction of hydrogen peroxide with cyclic ketones to afford ring-contracted carboxylic acids was first reported in 1957 by G. B. Payne et al. (J. Org. Chem., 22, 1680 1957). In 1959 H. M. Hellman et al. reported in Tetrahedron Letters, 1 (1959) the formation of Baeyer-Villiger products, that is, cyclic lactones by employing selenic acid ($H_2SeO_4$) rather than selenium dioxide as the catalyst. However they also obtained the ring-contracted carboxylic acids. Subsequent efforts to oxidize cyclic ketones up till the present time have afforded the same mixtures of cyclic lactones and ring-contracted carboxylic acid.

Commercially one of the most important applications of the oxidation of cyclic ketones to cyclic lactones is that of the conversion of cyclohexanone to epsilon-caprolactone. Japanese Pat. No. 6,910,243 (Chem Abstracts, 71, 60755a 1969) discloses the Baeyer-Villiger oxidation of cyclohexanone to epsilon-caprolactone using 30 percent aqueous hydrogen peroxide catalyzed by arsenic trioxide. An efficiency based on hydrogen peroxide of 74% was obtained and a conversion to the lactone of 64 percent. The Japanese Pat. No. 7007549 (Chemical Abstracts, 73, 14219x, 1970) describes the selenious acid ($H_2SeO_3$)-catalyzed oxidation of cyclohexanone with hydrogen peroxide at low temperatures, that is, less than 23° C. An efficiency of 11.2 percent to caprolactone based on 30 percent aqueous hydrogen peroxide was described together with a selectivity of lactone production of 58 percent.

It is believed that there are basically three methods of effecting the conversion of cyclohexanone to epsilon-caprolactone on a commercial scale. These are the direct oxidation of cyclohexanone with peracetic acid using ethyl acetate or acetone described in U.S. Pat. No. 3,522,279; the direct oxidation of cyclohexanone with aqueous peracetic acid (prepared from acetic acid and hydrogen peroxide-Netherlands patent application 6,613,409, Chemical Abstracts 67 63845h, (1967); or the direct oxidation of cyclohexanone with aqueous performic acid (French Pat. No. 1,385,557; Chemical Abstracts 62, 13051e, 1965); the co-oxidation of aldehyde and cyclohexanone described in several references including Netherlands patent application No. 6,409,489 (Chemical Abstracts, 63, 8208f, 1965); and the oxidation of cyclohexanone with t-butyl hydroperoxide, catalyzed by boric anhydride, described in German Offenlegungschrift No. 2,253,963 (Chemical Abstract, 79, 456r, 1973).

While the above three described methods are commercial, they suffer in common the disadvantage of organic by-product formation. The economics of these processes are also dependent on the relative costs of the oxidants and their reduction products, viz., carboxylic acid from the first and second methods and t-butyl alcohol from the third method. This is especially significant in the case of the second method which at best produces nearly two moles of carboxylic acid per mole of epsilon-caprolactone.

Two variations of the first method described above have also been considered commercially, viz., the oxidation of cyclohexanone with peracetic acid using water as a solvent (Netherlands application No. 6,613,409; Chemical Abstract 67, 63845h, 1967) and the oxidation of cyclohexanone with aqueous performic acid (French patent 1,385,557; Chem. Abstracts, 62, 13051e, 1965).

These methods however also suffer the disadvantage of requiring the recycle of large amounts of carboxylic acids and the use of the concentrated hydrogen peroxide.

There is therefore still a continuing need in this art for a method of oxidizing cyclohexanone to epsilon-caprolactone with a minimum of by-product formation.

SUMMARY OF THE INVENTION

It has now been found that cycloaliphatic ketones containing from about 5 to about 7 carbon atoms inclusive can be converted to the corresponding lactone in high yield by oxidation of said ketone with hydrogen peroxide and a catalytic amount of a selenium compound having a valence of +4, selected from the group consisting of selenium dioxide, selenious acid, alkali metal salts of selenious acid, selenium halides, selenium oxyhalides, and dialkyl selenites having 1 to about 10 carbon atoms in each alkyl moiety, in the presence of at least about 0.1 equivalent weight, per equivalent weight of said selenium compound, of a base having a conjugate acid with a dissociation constant in the range of about $5 \times 10^{-8}$ to about $8 \times 10^{-2}$. Although temperatures of about 20° C. to about 200° C. can be used, temperatures of about 40° C. to about 100° C. are preferred.

The term "halides" includes fluorides, chlorides, bromides an iodides.

The term "equivalent weight" is defined in the Condensed Chemical Dictionary 7th Edition, A. and C. Rose, Reinhold Publishing Corp., NYC 1966 as the weight that will combine with one atomic weight of hydrogen or replce one-half atomic weight of oxygen.

The term "conjugate acid" is defined in "Physical Organic Chemistry" by L. P. Hammett, page 48–49, McGraw Hill Book Co. NYC 1940.

In this case a substance that accepts a proton through an unshared pair of electrons is a base, and the product of the base plus a proton is an acid. The acid and base related this way are described as being conjugate or corresponding.

Although this conversion of ketone to lactone can be carried out in situ, in one step, it is preferred to first form and isolate the adduct reaction product of hydrogen peroxide and ketone, such as, the 1,1'-dihydroxydicycloalkyl peroxide and then convert this to lactone in the presence of a selenium compound, such as, selenium dioxide, and a base. This reaction of hydrogen peroxide and ketone can also produce other products. Thus in the case of cyclohexanone it can be a 1-hydroperoxycyclohexanol, 1,1-dihydroperoxycyclohexane, 1,1′-dihydroxydicyclohexyl peroxide, 1-hydroxy-1′-hydroperoxydicyclohexyl peroxide, 1,1′-dihydroperoxydicyclohexyl peroxide, dicyclohexylidene diperoxide, tricyclohexylidene triperoxide, and the like.

While not wishing to be bound by any theory or mechanism of reaction, it is believed that this unexpected result is possible because the above-mentioned selenium compounds in the +4 valence state do not catalyze ring-contractive oxidation to by-products whereas selenium in the +6 valence state catalyzes both reaction routes, that is, leads to a mixture of both lactone and carboxylic acid by-product.

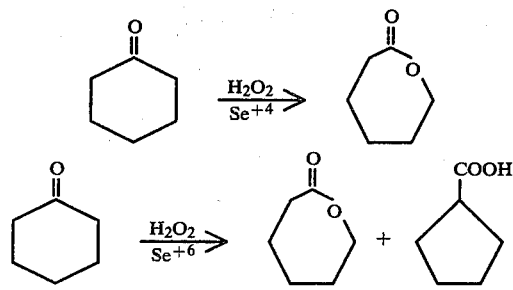

Selenium dioxide is the preferred catalyst for this reaction. The criticality of the catalyst is demonstrated by the fact that other selenium compounds such as selenic acid, diphenylselenide, diphenylselenoxide, benzeneseleninic acid and other selenium compounds do not afford the specificity of the +4 valence selenium catalysts enumerated above.

Suitable inert solvents include normally liquid aliphatic and cycloaliphatic ethers, benzene and its alkyl or halogen substituted derivatives and the like. A preferred cycloaliphatic ether is 1,4-dioxane.

The agent which has been discovered to inhibit the activity of selenium species in the +6 valence state can be generally described as a base although combinations of reagents which react to form weak bases can also be used, e.g., lithium selenite (dibasic) plus acetic, formic, or oxalic acids; alkali metal hydroxides such as lithium hydroxide plus acetic acid; alkali metal oxalates (dibasic) plus oxalic acid, and the like. The solubility characteristics of the additive in the reaction medium determine the effectiveness of the base in suppressing the activity of +6 selenium without inhibiting the activity of the selenium catalyst in the +4 state. Thus the combination of potassium oxalate and oxalic acid results in significantly lower reaction efficiency that that of lithium oxalate and oxalic acid, when 1,4-dioxane is used as a solvent. It is preferred to add the selenium compound in two portions for enhanced yields.

By catalytic amounts of a selenium compound is meant at least about 0.1 mole % of selenium compound based on the moles of hydrogen peroxide charged.

Other bases which are effective include pyridine, piperidine, as well as other aromatic basic nitrogen-containing compounds. Aliphatic and cycloaliphatic nitrogen-containing compounds, such as, mono-, di-, and trialkylamines having 1 to 10 carbon atoms and cyclopentylamine and cyclohexylamine and N-substituted alkyl derivatives thereof can also be used. Still another variation is the use of basic ion exchange resins.

The use of a base to achieve the controlled reaction sequence described above is quite unexpected. The obvious expedient of using a reducing agent to keep selenium dioxide in the +4 valence state is unworkable because the selenium would be reduced down to selenium metal with 0 valence. Selenium in this valence state is not a catalyst for the conversion of cyclic ketones to cyclic esters.

The method of this invention can be practiced in a continuous or a batch system or a combination of both.

Pressure is not critical although atmospheric pressures are preferred for reasons of economy.

Time is not critical. For practical yields reaction times of 4–6 hours are preferred.

The invention is further disclosed in the Examples which follow. All parts and percentages are by weight unless otherwise specified.

EXAMPLE 1

Preparation of 1,1′-Dihydroxydicyclohexyl Peroxide

In a 200 ml, 3-neck round-bottom flask equipped with a magnetic stirring bar, two addition funnels, and a thermometer, was placed 20.45 ml. of 30% hydrogen peroxide. One addition funnel was charged with 41.3 ml. of distilled cyclohexanone and the other with 82.6 ml of water. The contents of the two addition funnels were discharged gradually and constantly into the stirred round-bottom flask whose contents were kept at a constant temperature of about 25°–26° C. No exothermicity was noted. After both addition funnels were emptied into the round-bottom flask stirring was continued overnight.

Crystals of 1,1′-dihydroxydicyclohexyl peroxide were filtered with suction from the round-bottom flask, washed and dried on the filter. After futher drying in vacuo, the yield of 1,1′-dihydroxydicyclohexyl peroxide was determined to be 30.5 g. This preparation is described in Zhurnal Prikladnoi Khimii, Vol. 40, No. 11, pp. 2555–2561, November 1967.

CONTROL 1

Conversion of 1,1′-Dihydroxydicyclohexyl Peroxide to Epsilon-Caprolactone

A mixture of 3.45 grams (15 millimoles) of 1,1′-dihydroxycyclohexyl peroxide (prepared as in Example 1), 41 mg. of selenium dioxide and 0.543 grams of chlorobenzene (internal standard for gas chromatographic analysis), in 20 ml. of dioxane (purified by distillation from sodium metal), was heated at 60° C. for 3 hours. Analysis of the product mixture by gas chromatography showed it to contain 5.2 millimoles of epsilon-caprolactone (35% of theory) and 3.7 millimoles of cyclopentanecarboxylic acid (25% of theory). The gas chromatographic analysis was conducted with a Carbowax 20 M column (a tradename of Union Carbide for ethylene oxide polymer having a molecular weight of about 20 thousand), with a column temperature programmed from 80° to 160° C.

EXAMPLE 2

Conversion of 1,1'-Dihydroxydicyclohexyl Peroxide to Epsilon-Caprolactone in the Presence of Pyridine as a Base Control 1 was repeated with the exception that a 0.12 gram portion of pyridine (1.5 millimoles) was added to the reaction mixture. The mixture was heated at 60° C. with stirring for 4 hours after which time an additional 41 mg portion of selenium dioxide was then added and heating continued for 2 additional hours. Gas chromatographic analysis of the product mixture revealed it to contain 6.2 millimoles (41% of theory) of epsilon-caprolactone and 3.0 millimoles (20% of theory) of cyclopentanecarboxylic acid.

EXAMPLE 3

Conversion of 1,1'-Dihydroxydicyclohexyl Peroxide to Epsilon-Caprolactone in the Presence of Lithium Hydroxide/Acetic Acid as the Base A mixture of 1.75 grams (7.6 millimoles) of 1,1'-dihydroxydicyclohexyl peroxide (prepared as in Example 1), 20 mg of selenium dioxide, 64 mg of lithium hydroxide dihydrate, 100 microliters of glacial acetic acid, and 0.523 grams of chlorobenzene in 10 ml of dioxane was heated with stirring for 4 hours at 60° C. A second 20 mg portion of selenium dioxide was added after the first two hours of heating. Analysis of the product by gas chromatography showed the product mixture to contain 5.7 millimoles of epsilon-caprolactone (75% of theory) and 0.4 millimoles of cyclopentane carboxylic acid.

EXAMPLE 4

Conversion of 1,1'-Dihydroxydicyclohexyl Peroxide to Epsilon-Caprolactone in the Presence of Lithium Oxalate and Oxalic Acid as the Base A reaction mixture consisting of 1.75 grams (7.6 millimoles) of 1,1'-dihydroxydicyclohexyl peroxide (prepared as in Example 1), 17 mg of selenium dioxide, 19 mg of oxalic acid, 16 mg of lithium oxalate (dibasic), and 0.523 grams of chlorobenzene in 10 ml of dioxane was heated with stirring for 3 hours at 60° C. A second 17 mg portion of selenium dioxide was then added and the mixture heated for 24 hours. Analysis by gas chromatography revealed the mixture to contain 6.5 millimoles of epsilon-caprolactone (85% of theory) and 0.8 millimoles of cyclopentanecarboxylic acid.

EXAMPLE 5

Conversion of 1,1'-Dihydroxydicyclohexyl Peroxide to Epsilon-Caprolactone in the Presence of Lithium Selenite as the Base A reaction mixture consisting of 1.75 grams (7.6 millimoles) of 1,1'-dihydroxydicyclohexyl peroxide (prepared as in Example 1), 21 mg of lithium selenite (dibasic), 8.4 mg of selenium dioxide, 14 microliters of formic acid and 0.54 grams of chlorobenzene in 10 ml of dioxane was heated at 60° C. with stirring for 7.5 hours and left over night at room temperature. A second 8.4 mg portion of selenium dioxide was added and the mixture was heated at 60° C. for 3 additional hours. Analysis by gas chromtography revealed the product mixture to contain 6.7 millimoles of epsilon-caprolactone (89% of theory) and 0.6 millimoles of cyclopentanecarboxylic acid.

EXAMPLE 6

Direct Oxidation of Cyclohexanone to Epsilon-Caprolactone

A 0.38 mg portion of 96% hydrogen peroxide (15 millimoles) was added at room temperature to a stirred solution of 2.94 grams (30 millimoles) of cyclohexanone and 0.884 grams of chlorobenzene in 20 ml of dioxane. The mixture was heated at 60° C. for 15 minutes with continued stirring and to it was then added 0.25 grams of selenium dioxide-loaded synthetic mordenite powder, 14 mg (0.3 millimoles) of formic acid and 33 mg (0.3 millimoles) of selenium dioxide. Heating and stirring were continued for 2.5 hours after the above additions. The product mixture was shown by gas chromatographic analysis to contain 8.7 millimoles of epsilon-caprolactone (58% of theory) and 1.3 millimoles (8.7% of theory) of cyclopentanecarboxylic acid.

Although the invention has been described in its preferred forms with a certain degree of particularity, it is understood that the present disclosure of the preferred forms has been made only by way of example and that numerous changes may be resorted to without departing from the spirit and scope of the invention.

What is claimed is:

1. Method for the preparation of cycloaliphatic lactones which comprises oxidizing a cycloaliphatic ketone, having from about 5 to about 7 carbon atoms inclusive, with hydrogen peroxide and a catalytic amount of a selenium compound, having a valence of +4, selected from the group consisting of selenium dioxide, selenious acid, alkali metal salts of selenious acid, selenium halides, selenium oxyhalides, and dialkyl selenites having 1 to about 10 carbon atoms in each alkyl moiety, in the presence of at least 0.1 equivalent weights, per equivalent weight of selenium compound, of a base having a conjugate acid with a dissociation constant in the range of about $5 \times 10^{-8}$ to about $8 \times 10^{-2}$, in an inert solvent whereby the oxidation by +6 valence selenium of said aliphatic ketone is inhibited, at a temperature of about 20° C. to about 200° C.

2. Method claimed in claim 1 wherein a cycloaliphatic ketone/peroxide adduct is first isolated.

3. Method claimed in claim 2 wherein the cycloaliphatic ketone/peroxide adduct is a 1,1'-dihydroxydicycloalkyl peroxide.

4. Method claimed in claim 1 wherein the cycloaliphatic ketone is cyclohexanone.

5. Method claimed in claim 1 wherein the selenium compound is selenium dioxide.

6. Method claimed in claim 1 wherein the temperature is about 40° C. to about 100° C.

7. Method claimed in claim 1 wherein the selenium compound is charged in two portions.

8. Method claimed in claim 1 wherein the inert solvent is 1,4-dioxane.

9. Method claimed in claim 1 wherein the inert solvent is chlorobenzene.

10. Method claimed in claim 1 wherein the base is a mixture of lithium hydroxide and acetic acid.

11. Method claimed in claim 1 wherein the base is a mixture of lithium selenite and formic acid.

12. Method claimed in claim 1 wherein the cycloaliphatic ketone is oxidized in situ without isolation of cycloaliphatic ketone/peroxide adduct.

* * * * *